US012746014B2

(12) United States Patent
Bell et al.

(10) Patent No.: US 12,746,014 B2
(45) Date of Patent: Sep. 29, 2026

(54) SURGICAL RESECTION DEVICE AND METHODS OF OPERATION THEREOF

(71) Applicants: Smith & Nephew, Inc., Memphis, TN (US); Smith & Nephew Asia Pacific Pte. Limited, Singapore (SG); Smith & Nephew Orthopaedics AG, Zug (CH)

(72) Inventors: Brett J. Bell, Mendon, UT (US); Samuel C. Dumpe, Sewickley, PA (US)

(73) Assignees: Smith & Nephew, Inc., Memphis, TN (US); Smith & Nephew Asia Pacific Pte. Limited, Singapore (SG); Smith & Nephew Orthopaedics AG, Zug (CH)

( * ) Notice: Subject to any disclaimer, the term of this patent is extended or adjusted under 35 U.S.C. 154(b) by 30 days.

(21) Appl. No.: 18/580,375

(22) PCT Filed: Jul. 19, 2022

(86) PCT No.: PCT/US2022/037553
§ 371 (c)(1),
(2) Date: Jan. 18, 2024

(87) PCT Pub. No.: WO2023/003849
PCT Pub. Date: Jan. 26, 2023

(65) Prior Publication Data

US 2024/0252179 A1 Aug. 1, 2024

Related U.S. Application Data

(60) Provisional application No. 63/223,233, filed on Jul. 19, 2021.

(51) Int. Cl.
*A61B 17/14* (2006.01)
*A61B 17/16* (2006.01)
*A61B 34/20* (2016.01)

(52) U.S. Cl.
CPC ........ *A61B 17/142* (2016.11); *A61B 17/1615* (2013.01); *A61B 17/1626* (2013.01); *A61B 34/20* (2016.02); *A61B 2034/2055* (2016.02)

(58) Field of Classification Search
CPC ..... A61B 17/14; A61B 17/142; A61B 17/144; A61B 17/16; A61B 17/1613;
(Continued)

(56) References Cited

U.S. PATENT DOCUMENTS 6,757,582 B2 * 6/2004 Brisson .................. B33Y 50/02 83/768
10,492,870 B2 * 12/2019 Shalayev ............... A61B 90/36
(Continued)

FOREIGN PATENT DOCUMENTS

EP 3824823 A1 * 5/2021 ............. A61B 34/30
WO WO-2011133927 A2 * 10/2011 ............. A61B 34/20
(Continued)

*Primary Examiner* — Eric S Gibson
(74) *Attorney, Agent, or Firm* — ArentFox Schiff LLP; Joseph M. Maraia

(57) ABSTRACT

Surgical methods and devices that facilitate anatomical resection are disclosed. In some examples, a surgical resection device is disclosed that includes a static housing and a resection tool coupled to the housing via a flexible gasket that allows relative motion between the static housing and resection tool. A motor is also coupled to the static housing and is configured to rotate the resection tool about a first axis. The surgical resection device also includes two linear actuators disposed within a handle and coupled to the static housing via respective pinned linkages. The actuators are independently drivable to translate the resection tool within a second axis and rotate the resection tool about a third axis. A surgical computing device can track the surgical resection device, drive the motor and actuators to align the resection
(Continued)

tool with a resection plane determined preoperatively, and control a position and speed of the resection tool.

11 Claims, 6 Drawing Sheets

(58) Field of Classification Search

CPC .............. A61B 17/1615; A61B 17/162; A61B 17/1622; A61B 17/1624; A61B 17/1626; A61B 17/1628; A61B 17/1633; A61B 2017/00367; A61B 2017/00398; A61B 2017/00402; A61B 34/20; A61B 2034/2055; A61B 2034/2057

See application file for complete search history.

(56) References Cited

U.S. PATENT DOCUMENTS

| | | | | |
|---|---|---|---|---|
| 11,471,170 | B1 * | 10/2022 | Nikou | A61B 34/20 |
| 11,517,380 | B2 | 12/2022 | Kang et al. | |
| 11,648,679 | B2 | 5/2023 | Bowling et al. | |
| 11,911,117 | B2 * | 2/2024 | Haider | A61B 90/39 |
| 11,931,267 | B2 * | 3/2024 | Wilde | A61B 34/30 |
| 12,310,671 | B2 * | 5/2025 | Bell | G16H 50/50 |
| 2003/0208296 | A1 * | 11/2003 | Brisson | A61B 90/10 700/117 |
| 2011/0264107 | A1 * | 10/2011 | Nikou | A61B 17/1633 700/258 |
| 2013/0096574 | A1 * | 4/2013 | Kang | A61B 34/30 606/130 |
| 2016/0022374 | A1 * | 1/2016 | Haider | A61B 17/142 606/96 |
| 2016/0113720 | A1 * | 4/2016 | Lavallee | A61B 17/15 901/9 |
| 2016/0199072 | A1 * | 7/2016 | Torrie | A61B 1/0014 606/80 |
| 2017/0258532 | A1 * | 9/2017 | Shalayev | A61B 17/1624 |
| 2018/0185052 | A1 * | 7/2018 | Zhou | A61B 17/320068 |
| 2020/0121400 | A1 * | 4/2020 | Girardeau-Montaut | A61B 34/37 |
| 2020/0375613 | A1 * | 12/2020 | Frey | A61B 17/1626 |
| 2021/0186614 | A1 * | 6/2021 | Forstein | G16H 20/40 |
| 2021/0204963 | A1 * | 7/2021 | Mitra | A61B 34/20 |
| 2021/0353431 | A1 * | 11/2021 | Wilde | A61B 34/30 |
| 2022/0015773 | A1 * | 1/2022 | Chappuis | A61B 17/155 |
| 2022/0071713 | A1 | 3/2022 | Zuhars | |
| 2022/0257263 | A1 * | 8/2022 | Chappuis | A61B 17/142 |
| 2022/0273396 | A1 | 9/2022 | Bozung et al. | |
| 2022/0304829 | A1 | 9/2022 | Otto et al. | |
| 2022/0338935 | A1 * | 10/2022 | Bell | G16H 20/40 |
| 2022/0409298 | A1 * | 12/2022 | Haider | A61B 34/37 |
| 2023/0068121 | A1 | 3/2023 | Lindeman et al. | |
| 2023/0255701 | A1 | 8/2023 | Post et al. | |
| 2024/0090957 | A1 | 3/2024 | Bozung | |
| 2024/0108358 | A1 | 4/2024 | VanDyken et al. | |
| 2024/0252179 | A1 * | 8/2024 | Bell | A61B 34/20 |

FOREIGN PATENT DOCUMENTS

| | | | | | |
|---|---|---|---|---|---|
| WO | WO-2014198784 | A1 * | 12/2014 | A61B 17/1764 |
| WO | WO-2016049180 | A1 * | 3/2016 | A61B 17/1691 |
| WO | WO-2019222728 | A1 * | 11/2019 | A61B 34/20 |
| WO | WO-2019226824 | A1 * | 11/2019 | G16H 40/67 |
| WO | WO-2020257444 | A1 * | 12/2020 | A61B 34/30 |
| WO | WO-2021113227 | A1 * | 6/2021 | A61B 34/10 |
| WO | WO-2021231994 | A1 * | 11/2021 | A61B 34/32 |
| WO | 2022147001 | A1 | 7/2022 | |
| WO | WO-2023003849 | A1 * | 1/2023 | A61B 17/1626 |
| WO | 2023136930 | A1 | 7/2023 | |
| WO | 2023141265 | A1 | 7/2023 | |
| WO | 2024020088 | A1 | 1/2024 | |

* cited by examiner

SURGICAL RESECTION DEVICE AND METHODS OF OPERATION THEREOF

CROSS-REFERENCE TO RELATED APPLICATIONS

This application is a U.S. national stage filing under 35 U.S.C. § 371 of International Patent Application No. PCT/US2022/037553, filed Jul. 19, 2022, entitled "SURGICAL RESECTION DEVICE AND METHODS OF OPERATION THEREOF." which claims priority to U.S. provisional application Ser. No. 63/223,233, filed Jul. 19, 2021 and entitled, "SURGICAL RESECTION DEVICE AND METHODS OF OPERATION THEREOF," each of which is incorporated herein by reference in their entirety.

TECHNICAL FIELD

The present disclosure relates generally to methods, systems, and apparatuses related to a computer-assisted surgical system that includes various hardware and software components that work together to enhance surgical workflows. The disclosed techniques may be applied to, for example, shoulder, hip, and knee arthroplasties, as well as other surgical interventions such as arthroscopic procedures, spinal procedures, maxillofacial procedures, rotator cuff procedures, ligament repair and replacement procedures.

BACKGROUND

Resection of bone for arthroplasty procedures (e.g., total knee replacements) is commonly done using an oscillating saw and cutting guide(s) aligned manually using anatomical references. More recently, robotic or computer assisted arthroplasty has improved accuracy and repeatability of resection and implant placement and associated patient outcomes. In particular, postoperative function, pain, rehabilitation, and satisfaction can all be influenced by the placement of the implant.

However, a significant disadvantage of computer assisted arthroplasty procedures is the size and cost of the robotics systems necessary for performing the procedures. Additionally, many of these robotic systems remove control from the surgeon performing the procedure. In order to overcome these limitations, a handheld surgical device is presented which is configured to automatically align a cutting implement, cutting block, or implant with multiple degrees of freedom.

SUMMARY

Surgical computing devices, surgical resection device, surgical, systems, non-transitory computer readable media, and surgical methods that facilitate improved resection of patient anatomy during surgical procedures are disclosed. According to some embodiments, a surgical resection device includes a static housing and a resection tool comprising an annular gear and coupled to the static housing via a flexible gasket that allows relative motion between the static housing and resection tool. A motor is coupled to the static housing and comprises a pinion gear configured to interface with the annular gear to rotate the resection tool about a first axis. A handle coupled to the static housing and at least two linear actuators disposed within the handle and coupled to the static housing via respective pinned linkages. The at least two linear actuators are independently drivable to translate the resection tool within a second axis and rotate the resection tool about a third axis.

According to some embodiments, the second axis is different than the first axis and the third axis is different than each of the first axis and the second axis.

According to some embodiments, the at least two linear actuators comprise first and second linear actuators spaced from each other in a direction of the first axis.

According to some embodiments, each of the at least two linear actuators comprises another motor and a nut or lead screw assembly.

According to some embodiments, one or more of the at least two linear actuators comprises a pneumatic actuator, a hydraulic actuator, or a piezo-electric actuator.

According to some embodiments, the surgical resection device further comprises an optical tracking device coupled to the static housing and comprising a plurality of fiducials.

According to some embodiments, the resection tool comprises a burr, a sagittal surgical saw, or an oscillating surgical saw.

According to some embodiments, the motor is further configured to extend and retract the resection tool along a direction of the first axis.

According to some embodiments, the resection tool is removable from the static housing.

According to some embodiments, the at least two linear actuators and the motor are collectively configured to control the resection tool in three degrees of freedom.

According to some embodiments, a surgical computing device is disclosed that comprises a non-transitory computer readable medium comprising programmed instructions stored thereon for facilitating resection during a surgical procedure and one or more processors coupled to the non-transitory computer-readable medium and configured to execute the stored programmed instructions to determine a resection plane for resecting patient anatomy based on a preoperative surgical plan. A position and orientation of a surgical resection device is then tracked during a surgical procedure. The surgical resection device comprises a resection tool, a motor configured to rotate the resection tool about a first axis, and at least two linear actuators independently drivable to translate the resection tool within a second axis and rotate the resection tool about a third axis. One or more of the motor or one or more of the at least two linear actuators are driven to align a portion of the resection tool with the resection plane based on the tracked position and orientation. A position of the portion of the resection tool in a direction of the first axis, or a speed of the portion of the resection tool, is controlled based on the tracked position and orientation during resection of the patient anatomy.

According to some embodiments, the resection tool comprises a surgical saw, wherein the portion of the surgical saw comprises a saw blade.

According to some embodiments, the one or more processors are further configured to execute the stored programmed instructions to initiate oscillation of the saw blade when an alignment of the saw blade with the resection plane is determined to be achieved based on the tracked position and orientation.

According to some embodiments, the one or more processors are further configured to execute the stored programmed instructions to enable or disable oscillation of the saw blade to control the position of the saw blade in the direction of the first axis.

According to some embodiments, the one or more processors are further configured to execute the stored programmed instructions to extend or limit oscillation of the saw blade to control the position of the saw blade in the direction of the first axis.

According to some embodiments, the one or more processors are further configured to execute the stored programmed instructions to retract the saw blade into, or extend the saw blade from, a sleeve disposed within a static housing of the surgical resection device to control the position of the saw blade in the direction of the first axis.

According to some embodiments, the resection tool and the motor are disposed proximate opposing ends of the static housing and interface within the static housing via an annular gear of the resection tool and a pinion gear of the motor. In these embodiments, the processors are further configured to execute the stored programmed instructions to drive the motor to rotate the pinion gear to cause the pinion gear to engage the annular gear to rotate the resection tool about the first axis.

According to some embodiments, the one or more processors are further configured to execute the stored programmed instructions to track the position and orientation relative to the patient anatomy based on a first optical tracking device coupled to the surgical resection device and a second optical tracking device coupled to the patient anatomy. In these embodiments, each of the first and second optical tracking devices comprises a plurality of fiducials.

According to some embodiments, the resection tool comprises a burr. In these embodiments, the processors are further configured to execute the stored programmed instructions to initiate rotation of the burr when an alignment of the burr with the resection plane is determined to be achieved based on the tracked position and orientation.

According to some embodiments, the one or more processors are further configured to execute the stored programmed instructions to extend or retract the burr in the direction of the first axis to control an exposure of the burr.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. In the drawings.

DETAILED DESCRIPTION

This disclosure is not limited to the particular systems, devices and methods described, as these may vary. The terminology used in the description is for the purpose of describing the particular versions or embodiments only and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

DEFINITIONS

For the purposes of this disclosure, the term "implant" is used to refer to a prosthetic device or structure manufactured to replace or enhance a biological structure. For example, in a total hip replacement procedure a prosthetic acetabular cup (implant) is used to replace or enhance a patients worn or damaged acetabulum. While the term "implant" is generally considered to denote a man-made structure (as contrasted with a transplant), for the purposes of this specification an implant can include a biological tissue or material transplanted to replace or enhance a biological structure.

For the purposes of this disclosure, the term "real-time" is used to refer to calculations or operations performed on-the-fly as events occur or input is received by the operable system. However, the use of the term "real-time" is not intended to preclude operations that cause some latency between input and response, so long as the latency is an unintended consequence induced by the performance characteristics of the machine.

Although much of this disclosure refers to surgeons or other medical professionals by specific job title or role, nothing in this disclosure is intended to be limited to a specific job title or function. Surgeons or medical professionals can include any doctor, nurse, medical professional, or technician. Any of these terms or job titles can be used interchangeably with the user of the systems disclosed herein unless otherwise explicitly demarcated. For example, a reference to a surgeon also could apply, in some embodiments to a technician or nurse.

The systems, methods, and devices disclosed herein are particularly well adapted for surgical procedures that utilize surgical navigation systems, such as the CORI® surgical navigation system. CORI is a registered trademark of BLUE BELT TECHNOLOGIES, INC. of Pittsburgh, PA, which is a subsidiary of SMITH & NEPHEW, INC. of Memphis, TN.

CASS Ecosystem Overview

Figure 1:
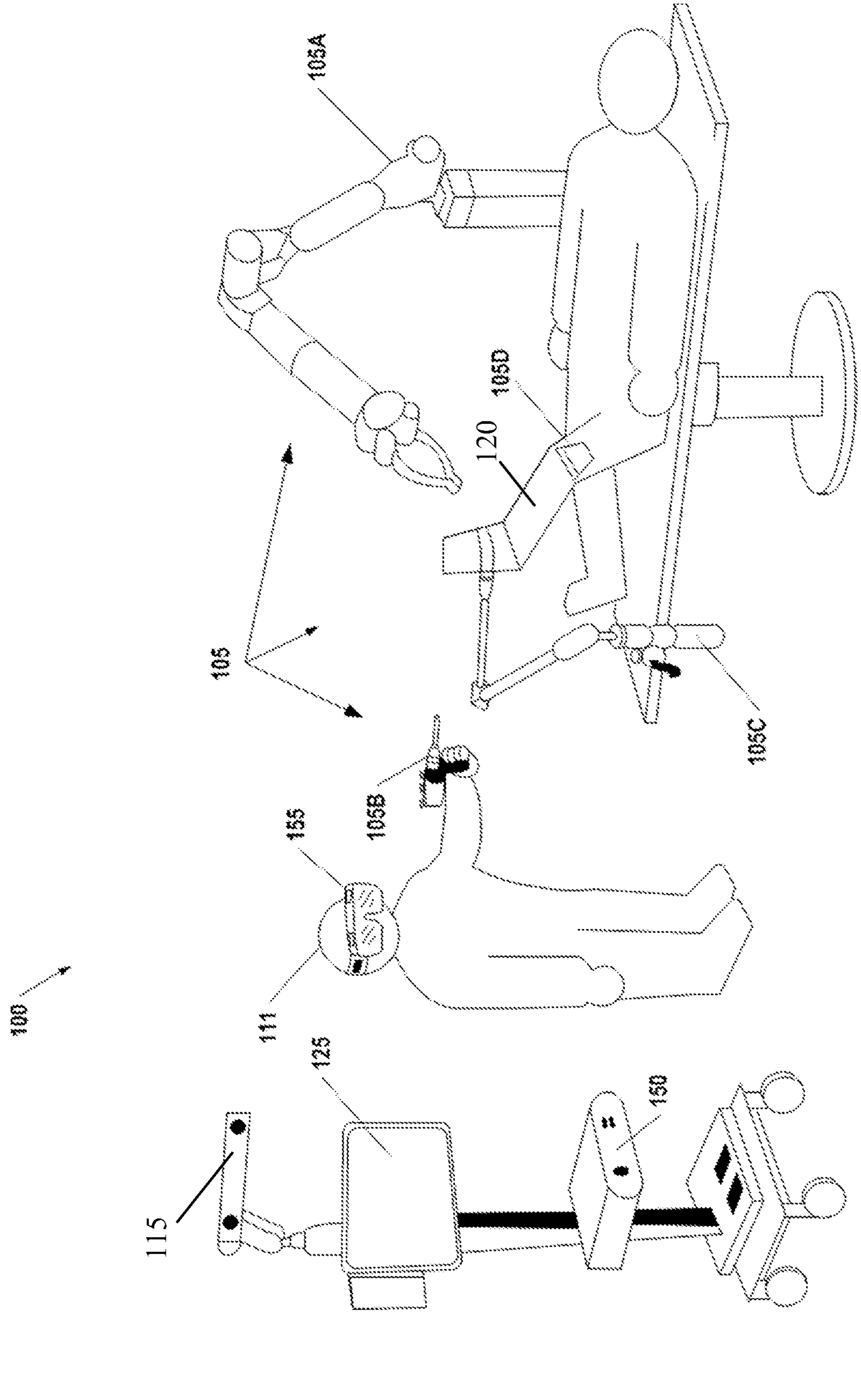
FIG. 1 depicts an operating theatre including an illustrative computer-assisted surgical system (CASS) in accordance with an embodiment.

FIG. 1 provides an illustration of an example computer-assisted surgical system (CASS) 100, according to some embodiments. As described in further detail in the sections that follow, the CASS uses computers, robotics, and imaging technology to aid surgeons in performing orthopedic surgery procedures such as total knee arthroplasty (TKA) or total hip arthroplasty (THA). For example, surgical navigation systems can aid surgeons in locating patient anatomical structures, guiding surgical instruments, and implanting medical devices with a high degree of accuracy. Surgical navigation systems such as the CASS 100 often employ various forms of computing technology to perform a wide variety of standard and minimally invasive surgical procedures and techniques. Moreover, these systems allow surgeons to more accurately plan, track and navigate the placement of instruments and implants relative to the body of a patient, as well as conduct pre-operative and intra-operative body imaging.

An Effector Platform 105 positions surgical tools relative to a patient during surgery. The exact components of the Effector Platform 105 will vary, depending on the embodiment employed. For example, for a knee surgery, the Effector Platform 105 may include an End Effector 105B that holds surgical tools or instruments during their use. The End Effector 105B may be a handheld device or instrument used by the surgeon (e.g., a CORI® hand piece or a cutting guide or jig) or, alternatively, the End Effector 105B can include a device or instrument held or positioned by a Robotic Arm 105A. While one Robotic Arm 105A is illustrated in FIG. 1, in some embodiments there may be multiple devices. As examples, there may be one Robotic Arm 105A on each side of an operating table T or two devices on one side of the table T. The Robotic Arm 105A may be mounted directly to the table T, be located next to the table T on a floor platform (not shown), mounted on a floor-to-ceiling pole, or mounted on a wall or ceiling of an operating room. The floor platform may be fixed or moveable. In one particular embodiment, the robotic arm 105A is mounted on a floor-to-ceiling pole located between the patient's legs or feet. In some embodiments, the End Effector 105B may include a suture holder or a stapler to assist in closing wounds. Further, in the case of two robotic arms 105A, the surgical computer 150 can drive the robotic arms 105A to work together to suture the wound at closure. Alternatively, the surgical computer 150 can drive one or more robotic arms 105A to staple the wound at closure.

The Effector Platform 105 can include a Limb Positioner 105C for positioning the patient's limbs during surgery. One example of a Limb Positioner 105C is the SMITH AND NEPHEW SPIDER2 system. The Limb Positioner 105C may be operated manually by the surgeon or alternatively change limb positions based on instructions received from the Surgical Computer 150 (described below). While one Limb Positioner 105C is illustrated in FIG. 1, in some embodiments there may be multiple devices. As examples, there may be one Limb Positioner 105C on each side of the operating table T or two devices on one side of the table T. The Limb Positioner 105C may be mounted directly to the table T, be located next to the table T on a floor platform (not shown), mounted on a pole, or mounted on a wall or ceiling of an operating room. In some embodiments, the Limb Positioner 105C can be used in non-conventional ways, such as a retractor or specific bone holder. The Limb Positioner 105C may include, as examples, an ankle boot, a soft tissue clamp, a bone clamp, or a soft-tissue retractor spoon, such as a hooked, curved, or angled blade. In some embodiments, the Limb Positioner 105C may include a suture holder to assist in closing wounds.

The Effector Platform 105 may include tools, such as a screwdriver, light or laser, to indicate an axis or plane, bubble level, pin driver, pin puller, plane checker, pointer, finger, or some combination thereof.

Resection Equipment 110 (not shown in FIG. 1) performs bone or tissue resection using, for example, mechanical, ultrasonic, or laser techniques. Examples of Resection Equipment 110 include drilling devices, burring devices, oscillatory sawing devices, vibratory impaction devices, reamers, ultrasonic bone cutting devices, radio frequency ablation devices, reciprocating devices (such as a rasp or broach), and laser ablation systems. In some embodiments, the Resection Equipment 110 is held and operated by the surgeon during surgery. In other embodiments, the Effector Platform 105 may be used to hold the Resection Equipment 110 during use.

The Effector Platform 105 also can include a cutting guide or jig 105D that is used to guide saws or drills used to resect tissue during surgery. Such cutting guides 105D can be formed integrally as part of the Effector Platform 105 or Robotic Arm 105A, or cutting guides can be separate structures that can be matingly and/or removably attached to the Effector Platform 105 or Robotic Arm 105A. The Effector Platform 105 or Robotic Arm 105A can be controlled by the CASS 100 to position a cutting guide or jig 105D adjacent to the patient's anatomy in accordance with a pre-operatively or intraoperatively developed surgical plan such that the cutting guide or jig will produce a precise bone cut in accordance with the surgical plan.

The Tracking System 115 uses one or more sensors to collect real-time position data that locates the patient's anatomy and surgical instruments. For example, for TKA procedures, the Tracking System may provide a location and orientation of the End Effector 105B during the procedure. In addition to positional data, data from the Tracking System 115 also can be used to infer velocity/acceleration of anatomy/instrumentation, which can be used for tool control. In some embodiments, the Tracking System 115 may use a tracker array attached to the End Effector 105B to determine the location and orientation of the End Effector 105B. The position of the End Effector 105B may be inferred based on the position and orientation of the Tracking System 115 and a known relationship in three-dimensional space between the Tracking System 115 and the End Effector 105B. Various types of tracking systems may be used in various embodiments of the present invention including, without limitation, Infrared (IR) tracking systems, electromagnetic (EM) tracking systems, video or image based tracking systems, and ultrasound registration and tracking systems. Using the data provided by the tracking system 115, the surgical computer 150 can detect objects and prevent collision. For example, the surgical computer 150 can prevent the Robotic Arm 105A and/or the End Effector 105B from colliding with soft tissue.

Any suitable tracking system can be used for tracking surgical objects and patient anatomy in the surgical theatre. For example, a combination of IR and visible light cameras can be used in an array. Various illumination sources, such as an IR LED light source, can illuminate the scene allowing three-dimensional imaging to occur. In some embodiments, this can include stereoscopic, tri-scopic, quad-scopic, etc. imaging. In addition to the camera array, which in some embodiments is affixed to a cart, additional cameras can be placed throughout the surgical theatre. For example, handheld tools or headsets worn by operators/surgeons can include imaging capability that communicates images back to a central processor to correlate those images with images captured by the camera array. This can give a more robust image of the environment for modeling using multiple perspectives. Furthermore, some imaging devices may be of suitable resolution or have a suitable perspective on the scene to pick up information stored in quick response (QR) codes or barcodes. This can be helpful in identifying specific objects not manually registered with the system. In some embodiments, the camera may be mounted on the Robotic Arm 105A.

In some embodiments, specific objects can be manually registered by a surgeon with the system preoperatively or intraoperatively. For example, by interacting with a user interface, a surgeon may identify the starting location for a tool or a bone structure. By tracking fiducial marks associated with that tool or bone structure, or by using other conventional image tracking modalities, a processor may track that tool or bone as it moves through the environment in a three-dimensional model.

In some embodiments, certain markers, such as fiducial marks that identify individuals, important tools, or bones in the theater may include passive or active identifiers that can be picked up by a camera or camera array associated with the tracking system. For example, an IR LED can flash a pattern that conveys a unique identifier to the source of that pattern, providing a dynamic identification mark. Similarly, one or two dimensional optical codes (barcode, QR code, etc.) can be affixed to objects in the theater to provide passive identification that can occur based on image analysis. If these codes are placed asymmetrically on an object, they also can be used to determine an orientation of an object by comparing the location of the identifier with the extents of an object in an image. For example, a QR code may be placed in a corner of a tool tray, allowing the orientation and identity of that tray to be tracked. Other tracking modalities are explained throughout. For example, in some embodiments, augmented reality headsets can be worn by surgeons and other staff to provide additional camera angles and tracking capabilities.

In addition to optical tracking, certain features of objects can be tracked by registering physical properties of the object and associating them with objects that can be tracked, such as fiducial marks fixed to a tool or bone. For example, a surgeon may perform a manual registration process whereby a tracked tool and a tracked bone can be manipulated relative to one another. By impinging the tip of the tool against the surface of the bone, a three-dimensional surface can be mapped for that bone that is associated with a position and orientation relative to the frame of reference of that fiducial mark. By optically tracking the position and orientation (pose) of the fiducial mark associated with that bone, a model of that surface can be tracked with an environment through extrapolation.

The registration process that registers the CASS 100 to the relevant anatomy of the patient also can involve the use of anatomical landmarks, such as landmarks on a bone or cartilage. For example, the CASS 100 can include a 3D model of the relevant bone or joint and the surgeon can intraoperatively collect data regarding the location of bony landmarks on the patient's actual bone using a probe that is connected to the CASS. Bony landmarks can include, for example, the medial malleolus and lateral malleolus, the ends of the proximal femur and distal tibia, and the center of the hip joint. The CASS 100 can compare and register the location data of bony landmarks collected by the surgeon with the probe with the location data of the same landmarks in the 3D model. Alternatively, the CASS 100 can construct a 3D model of the bone or joint without pre-operative image data by using location data of bony landmarks and the bone surface that are collected by the surgeon using a CASS probe or other means. The registration process also can include determining various axes of a joint. For example, for a TKA the surgeon can use the CASS 100 to determine the anatomical and mechanical axes of the femur and tibia. The surgeon and the CASS 100 can identify the center of the hip joint by moving the patient's leg in a spiral direction (i.e., circumduction) so the CASS can determine where the center of the hip joint is located.

A Tissue Navigation System 120 (not shown in FIG. 1) provides the surgeon with intraoperative, real-time visualization for the patient's bone, cartilage, muscle, nervous, and/or vascular tissues surrounding the surgical area. Examples of systems that may be employed for tissue navigation include fluorescent imaging systems and ultrasound systems.

The Display 125 provides graphical user interfaces (GUIs) that display images collected by the Tissue Navigation System 120 as well other information relevant to the surgery. For example, in one embodiment, the Display 125 overlays image information collected from various modalities (e.g., CT, MRI, X-ray, fluorescent, ultrasound, etc.) collected pre-operatively or intra-operatively to give the surgeon various views of the patient's anatomy as well as real-time conditions. The Display 125 may include, for example, one or more computer monitors. As an alternative or supplement to the Display 125, one or more members of the surgical staff may wear an Augmented Reality (AR) Head Mounted Device (HMD). For example, in FIG. 1 the Surgeon 111 is wearing an AR HMD 155 that may, for example, overlay pre-operative image data on the patient or provide surgical planning suggestions. Various example uses of the AR HMD 155 in surgical procedures are detailed in the sections that follow.

Surgical Computer 150 provides control instructions to various components of the CASS 100, collects data from those components, and provides general processing for various data needed during surgery. In some embodiments, the Surgical Computer 150 is a general purpose computer. In other embodiments, the Surgical Computer 150 may be a parallel computing platform that uses multiple central processing units (CPUs) or graphics processing units (GPU) to perform processing. In some embodiments, the Surgical Computer 150 is connected to a remote server over one or more computer networks (e.g., the Internet). The remote server can be used, for example, for storage of data or execution of computationally intensive processing tasks.

Various techniques generally known in the art can be used for connecting the Surgical Computer 150 to the other components of the CASS 100. Moreover, the computers can connect to the Surgical Computer 150 using a mix of technologies. For example, the End Effector 105B may connect to the Surgical Computer 150 over a wired (i.e., serial) connection. The Tracking System 115, Tissue Navigation System 120, and Display 125 can similarly be connected to the Surgical Computer 150 using wired connections. Alternatively, the Tracking System 115, Tissue Navigation System 120, and Display 125 may connect to the Surgical Computer 150 using wireless technologies such as, without limitation, Wi-Fi, Bluetooth, Near Field Communication (NFC), or ZigBee.

Robotic Arm

In some embodiments, the CASS 100 includes a robotic arm 105A that serves as an interface to stabilize and hold a variety of instruments used during the surgical procedure. For example, in the context of a hip surgery, these instruments may include, without limitation, retractors, a sagittal or reciprocating saw, the reamer handle, the cup impactor, the broach handle, and the stem inserter. The robotic arm 105A may have multiple degrees of freedom (like a Spider device), and have the ability to be locked in place (e.g., by a press of a button, voice activation, a surgeon removing a hand from the robotic arm, or other method).

In some embodiments, movement of the robotic arm 105A may be effectuated by use of a control panel built into the robotic arm system. For example, a display screen may include one or more input sources, such as physical buttons or a user interface having one or more icons, that direct movement of the robotic arm 105A. The surgeon or other healthcare professional may engage with the one or more input sources to position the robotic arm 105A when performing a surgical procedure.

A tool or an end effector 105B attached or integrated into a robotic arm 105A may include, without limitation, a burring device, a scalpel, a cutting device, a retractor, a joint tensioning device, or the like. In embodiments in which an end effector 105B is used, the end effector may be positioned at the end of the robotic arm 105A such that any motor control operations are performed within the robotic arm system. In embodiments in which a tool is used, the tool may be secured at a distal end of the robotic arm 105A, but motor control operation may reside within the tool itself.

The robotic arm 105A may be motorized internally to both stabilize the robotic arm, thereby preventing it from falling and hitting the patient, surgical table, surgical staff, etc., and to allow the surgeon to move the robotic arm without having to fully support its weight. While the surgeon is moving the robotic arm 105A, the robotic arm may provide some resistance to prevent the robotic arm from moving too fast or having too many degrees of freedom active at once. The position and the lock status of the robotic arm 105A may be tracked, for example, by a controller or the Surgical Computer 150.

In some embodiments, the robotic arm 105A can be moved by hand (e.g., by the surgeon) or with internal motors into its ideal position and orientation for the task being performed. In some embodiments, the robotic arm 105A may be enabled to operate in a "free" mode that allows the surgeon to position the arm into a desired position without being restricted. While in the free mode, the position and orientation of the robotic arm 105A may still be tracked as described above. In one embodiment, certain degrees of freedom can be selectively released upon input from user (e.g., surgeon) during specified portions of the surgical plan tracked by the Surgical Computer 150. Designs in which a robotic arm 105A is internally powered through hydraulics or motors or provides resistance to external manual motion through similar means can be described as powered robotic arms, while arms that are manually manipulated without power feedback, but which may be manually or automatically locked in place, may be described as passive robotic arms.

A robotic arm 105A or end effector 105B can include a trigger or other means to control the power of a saw or drill. Engagement of the trigger or other means by the surgeon can cause the robotic arm 105A or end effector 105B to transition from a motorized alignment mode to a mode where the saw or drill is engaged and powered on. Additionally, the CASS 100 can include a foot pedal (not shown) that causes the system to perform certain functions when activated. For example, the surgeon can activate the foot pedal to instruct the CASS 100 to place the robotic arm 105A or end effector 105B in an automatic mode that brings the robotic arm or end effector into the proper position with respect to the patient's anatomy in order to perform the necessary resections. The CASS 100 also can place the robotic arm 105A or end effector 105B in a collaborative mode that allows the surgeon to manually manipulate and position the robotic arm or end effector into a particular location. The collaborative mode can be configured to allow the surgeon to move the robotic arm 105A or end effector 105B medially or laterally, while restricting movement in other directions. As discussed, the robotic arm 105A or end effector 105B can include a cutting device (saw, drill, and burr) or a cutting guide or jig 105D that will guide a cutting device. In other embodiments, movement of the robotic arm 105A or robotically controlled end effector 105B can be controlled entirely by the CASS 100 without any, or with only minimal, assistance or input from a surgeon or other medical professional. In still other embodiments, the movement of the robotic arm 105A or robotically controlled end effector 105B can be controlled remotely by a surgeon or other medical professional using a control mechanism separate from the robotic arm or robotically controlled end effector device, for example using a joystick or interactive monitor or display control device.

The examples below describe uses of the robotic device in the context of a hip surgery; however, it should be understood that the robotic arm may have other applications for surgical procedures involving knees, shoulders, etc. One example of use of a robotic arm in the context of forming an anterior cruciate ligament (ACL) graft tunnel is described in WIPO Publication No. WO 2020/047051, filed Aug. 28, 2019, entitled "Robotic Assisted Ligament Graft Placement and Tensioning," the entirety of which is incorporated herein by reference.

A robotic arm 105A may be used for holding the retractor. For example in one embodiment, the robotic arm 105A may be moved into the desired position by the surgeon. At that point, the robotic arm 105A may lock into place. In some embodiments, the robotic arm 105A is provided with data regarding the patient's position, such that if the patient moves, the robotic arm can adjust the retractor position accordingly. In some embodiments, multiple robotic arms may be used, thereby allowing multiple retractors to be held or for more than one activity to be performed simultaneously (e.g., retractor holding & reaming).

The robotic arm 105A may also be used to help stabilize the surgeon's hand while making a femoral neck cut. In this application, control of the robotic arm 105A may impose certain restrictions to prevent soft tissue damage from occurring. For example, in one embodiment, the Surgical Computer 150 tracks the position of the robotic arm 105A as it operates. If the tracked location approaches an area where tissue damage is predicted, a command may be sent to the robotic arm 105A causing it to stop. Alternatively, where the robotic arm 105A is automatically controlled by the Surgical Computer 150, the Surgical Computer may ensure that the robotic arm is not provided with any instructions that cause it to enter areas where soft tissue damage is likely to occur. The Surgical Computer 150 may impose certain restrictions on the surgeon to prevent the surgeon from reaming too far into the medial wall of the acetabulum or reaming at an incorrect angle or orientation.

In some embodiments, the robotic arm 105A may be used to hold a cup impactor at a desired angle or orientation during cup impaction. When the final position has been achieved, the robotic arm 105A may prevent any further seating to prevent damage to the pelvis.

The surgeon may use the robotic arm 105A to position the broach handle at the desired position and allow the surgeon to impact the broach into the femoral canal at the desired orientation. In some embodiments, once the Surgical Computer 150 receives feedback that the broach is fully seated, the robotic arm 105A may restrict the handle to prevent further advancement of the broach.

The robotic arm 105A may also be used for resurfacing applications. For example, the robotic arm 105A may stabilize the surgeon while using traditional instrumentation and provide certain restrictions or limitations to allow for proper placement of implant components (e.g., guide wire placement, chamfer cutter, sleeve cutter, plan cutter, etc.). Where only a burr is employed, the robotic arm 105A may stabilize the surgeon's handpiece and may impose restrictions on the handpiece to prevent the surgeon from removing unintended bone in contravention of the surgical plan.

The robotic arm 105A may be a passive arm. As an example, the robotic arm 105A may be a CIRQ robot arm available from Brainlab AG. CIRQ is a registered trademark of Brainlab AG, Olof-Palme-Str. 9 81829, München, FED REP of GERMANY. In one particular embodiment, the robotic arm 105A is an intelligent holding arm as disclosed in U.S. patent application Ser. No. 15/525,585 to Krinninger et al., U.S. patent application Ser. No. 15/561,042 to Nowatschin et al., U.S. patent application Ser. No. 15/561,048 to Nowatschin et al., and U.S. Pat. No. 10,342,636 to Nowatschin et al., the entire contents of each of which is herein incorporated by reference.

Figure 2:
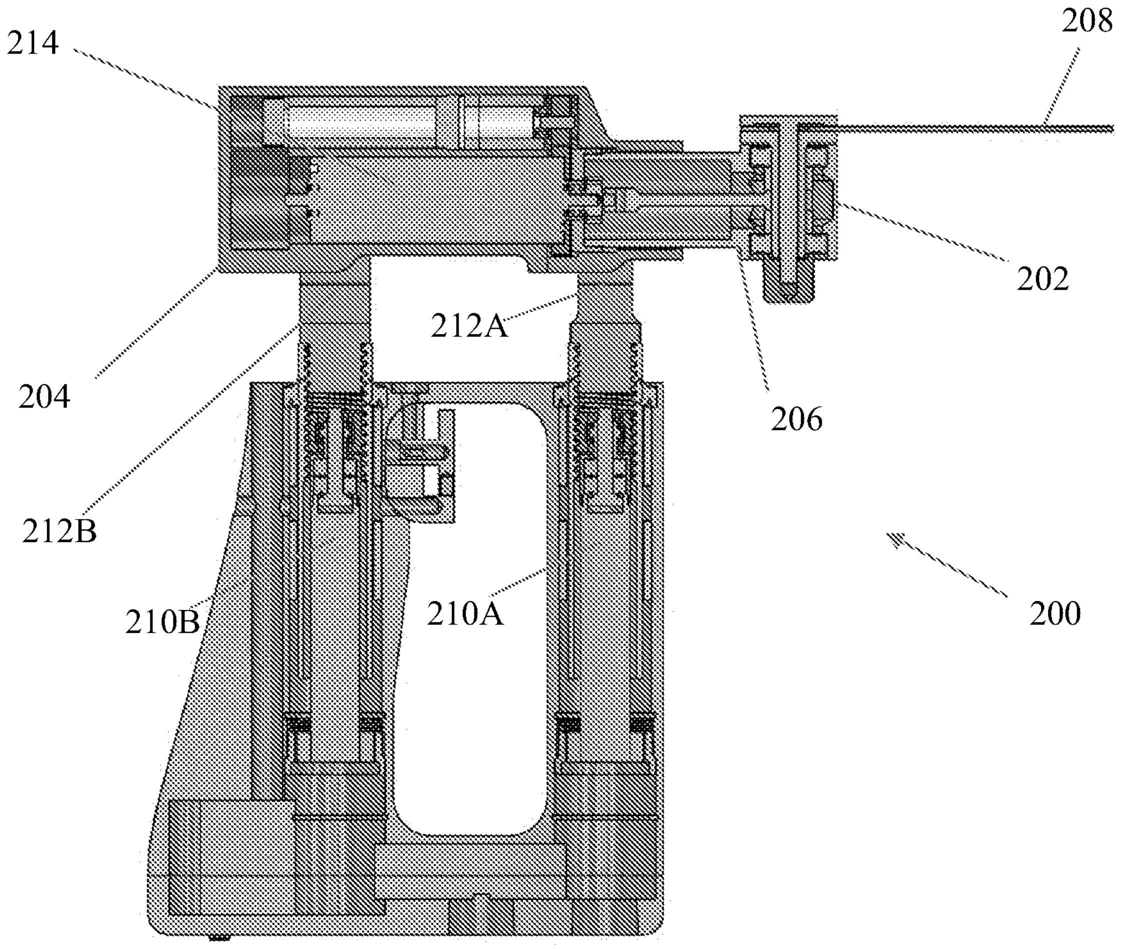
FIG. 2 depicts a surgical resection device in accordance with an embodiment.

Referring now to FIG. 2, a surgical resection device 200 in accordance with an embodiment of this technology is illustrated. The surgical resection device 200 in this example is handheld, has a minimum of two degrees of freedom, and is controlled through a navigation device in the CASS 100 to keep a cutting axis or plane constrained to a plane of interest, which is determined preoperatively and is referred to herein as a resection plane. The surgical resection device 200 is determined to be aligned with the resection plane based on a cutting element of a resection tool 202 of the surgical resection device that is coupled to a static housing 204 optionally via a flexible gasket 206. In the example illustrated in FIG. 2, the resection tool 202 is an oscillating surgical saw that has a saw blade 208 cutting element, but in other examples the resection tool can be another type of surgical saw (e.g., a sagittal surgical saw) or a burr, for example, and other types of cutting tools can also be used.

To constrain the resection tool 202 with respect to the resection plane, at least two linear actuators 210A-B are coupled to the static housing 204. The linear actuators 210A-B are capable of changing the position of the resection tool 202 in two degrees of freedom (i.e., a translational degree of freedom and a rotational degree of freedom). Accordingly, the linear actuators 210A-B restrain four degrees of freedom while actively controlling two degrees of freedom. The linear actuators 210A-B are coupled to the static housing 204 in this example via respective pinned linkages 212A-B and are spaced from each other in a direction of a first axis (i.e., the Z axis illustrated in FIG. 2). The linear actuators 210A-B are independently drivable to translate the resection tool 202 within a second axis (i.e., the Y axis illustrated in FIG. 2) and rotate the resection tool about a third axis (i.e., the X axis illustrated in FIG. 2).

In some examples, one or more of the linear actuators 210A-B can include a motor driving a nut that translates the rotational motion of the motor into a linear motion. In further examples, the nut is supported by a sleeve. In some examples, the nut is configured to at least partial envelop the motor in at least some states of the linear actuator.

Accordingly, in this example, the linear actuators 210A-B are driven independently to allow for translation in the direction of the Y axis as well as adjustment in roll via rotation about the X axis. The pinned linkages 212A-B therefore allow translation and rotation freedom in the Y direction and about the X axis, respectively. In some examples, the pinned linkages 212A-B are static. In an example, one or more of the pinned linkages 212A-B is configured to provide rotation while the other pinned linkage 212A-B is configured to provide rotation and translations (e.g., a slot and pin). One or more of the linear actuators 210A-B can be a direct current stepper motor coupled to a nut and/or a lead screw assembly, a pneumatic actuator, a hydraulic actuator, a piezo-electric actuator, a rack and pinion actuator, or an actuator based on a crank/arm or cam/follower mechanism, for example, although other types of actuators can be used in other examples.

In some examples, including as illustrated in FIG. 2, the resection tool 202 is further controlled in a third degree of freedom via a third rotational actuator, which is a motor 214 (e.g., a direct current stepper motor) coupled to the static housing 204 in this example, although another type of rotational actuator can also be used. The third degree of freedom therefore in this example is rotational and about the first axis (i.e., the Z axis illustrated in FIG. 2). In examples in which the cutting is performed by a burr, for example, the burr is inherently rotating about the first axis (i.e., the Z axis in FIG. 2) to affect the resection of the patient anatomy and therefore a third rotational degree of freedom about the first axis for the resection tool 202 itself is not provided.

Accordingly, control in a third degree of freedom can be provided in examples in which the resection tool 202 includes a saw blade 208, although the third degree of freedom can be controlled for other types of resection tools in other examples. In the example of the resection tool 202 with the saw blade 208 illustrated in FIG. 2, the motor 214 facilitates rotation of the saw blade about the long axis of the saw blade, which is referred to herein as the first axis and is the Z axis illustrated in FIG. 2. Therefore, in the example described and illustrated with reference to FIG. 2, the linear actuators 210A-B and motor 214 are collectively configured to control the resection tool 202 in three degrees of freedom.

To facilitate the rotation of the resection tool 202 about the first axis (i.e., the Z axis in FIG. 2), the resection tool in some examples includes an annular gear (not shown) and the resection tool is coupled to the static housing 204 via the flexible gasket 206 that allows relative motion between the static housing and the resection tool. In this example, the motor 214 includes a pinion gear (not shown) that is configured to interface, through or within the static housing 204, with the annular gear of the resection tool 202 to rotate the resection tool about the first axis (i.e., the Z axis in FIG. 2). In other words, actuation of the motor 214, and thus the pinion gear, drives rotation of the resection tool 202 and associated saw blade 208 within the static housing 204. Accordingly, in this example, the saw resection tool 202 (i.e., the oscillating surgical saw) is free to rotate in yaw (i.e., about the first axis or the Z axis illustrated in FIG. 2) relative to the static housing 204.

In yet other examples (e.g., in which the resection tool includes a burr), the third degree of freedom is translational and in the direction of the first axis (i.e., the Z axis illustrated in FIG. 2). In these examples the motor 214 or another linear actuator is configured to extend and retract the resection tool 202 along a direction of the first axis.

Optionally, the resection tool 202 can be removable from the static housing 204 in some examples. In these examples, particular degree(s) of freedom can be activated or inactivated based on the type or other characteristics of the installed resection tool 202. The activation or inactivation can be mechanical based on the connection or interface of the resection tool 202 (e.g., with respect to engagement with the motor 214 with the resection tool). In another example, the activation or inactivation can be electrical and managed by the surgical computer 150 or another device within the CASS 100 based on a determination of the type or other characteristics of the installed resection tool 202. Other methods for activating or inactivating degree(s) of freedom for particular installed resection tools can also be used in other examples.

Figure 3:
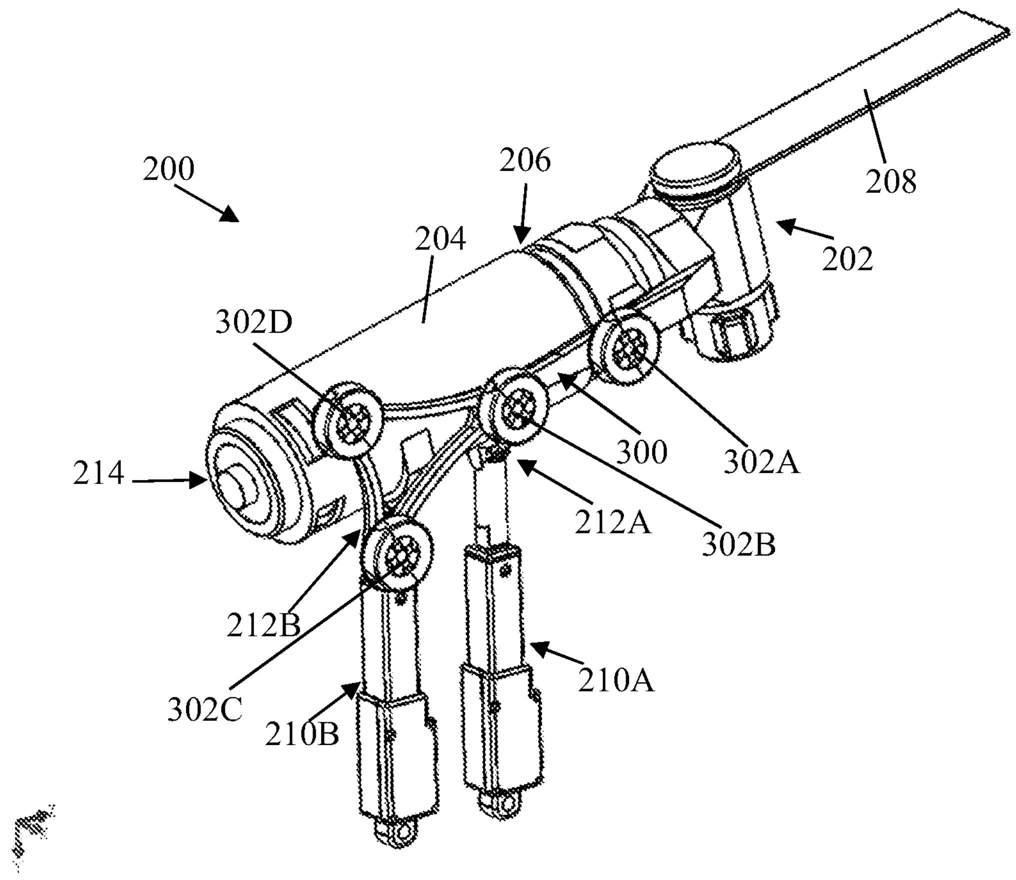
FIG. 3 depicts the surgical resection device of FIG. 2 coupled to an optical tracking system in accordance with an embodiment.

Referring to FIG. 3, the surgical resection device 200 is illustrated coupled to an optical tracking system 300 in accordance with an embodiment of this technology. The optical tracking system 300 in this example includes markers or fiducials 302A-D and is coupled to at least the static housing 204 of the surgical resection device 200. In this example, the position of the resection tool 202 can be determined based on motor encoders or other positions sensors. In other examples, the markers 302A-D can be coupled to mobile components (e.g., associated with the resection tool 202) with the actuation of the motor 214 and/or linear actuators 210A-B being based on the tracked position of the resection tool 202.

Other types of tracking devices can be used in other examples to track the position and orientation in space (e.g., the surgical environment) of the resection tool 202 by the CASS 100 and associated surgical computer 150 to facilitate control of the resection device 200 with respect to its position, orientation, activation, and/or speed, as described and illustrated in more detail below with reference to FIG. 5.

Figure 4:
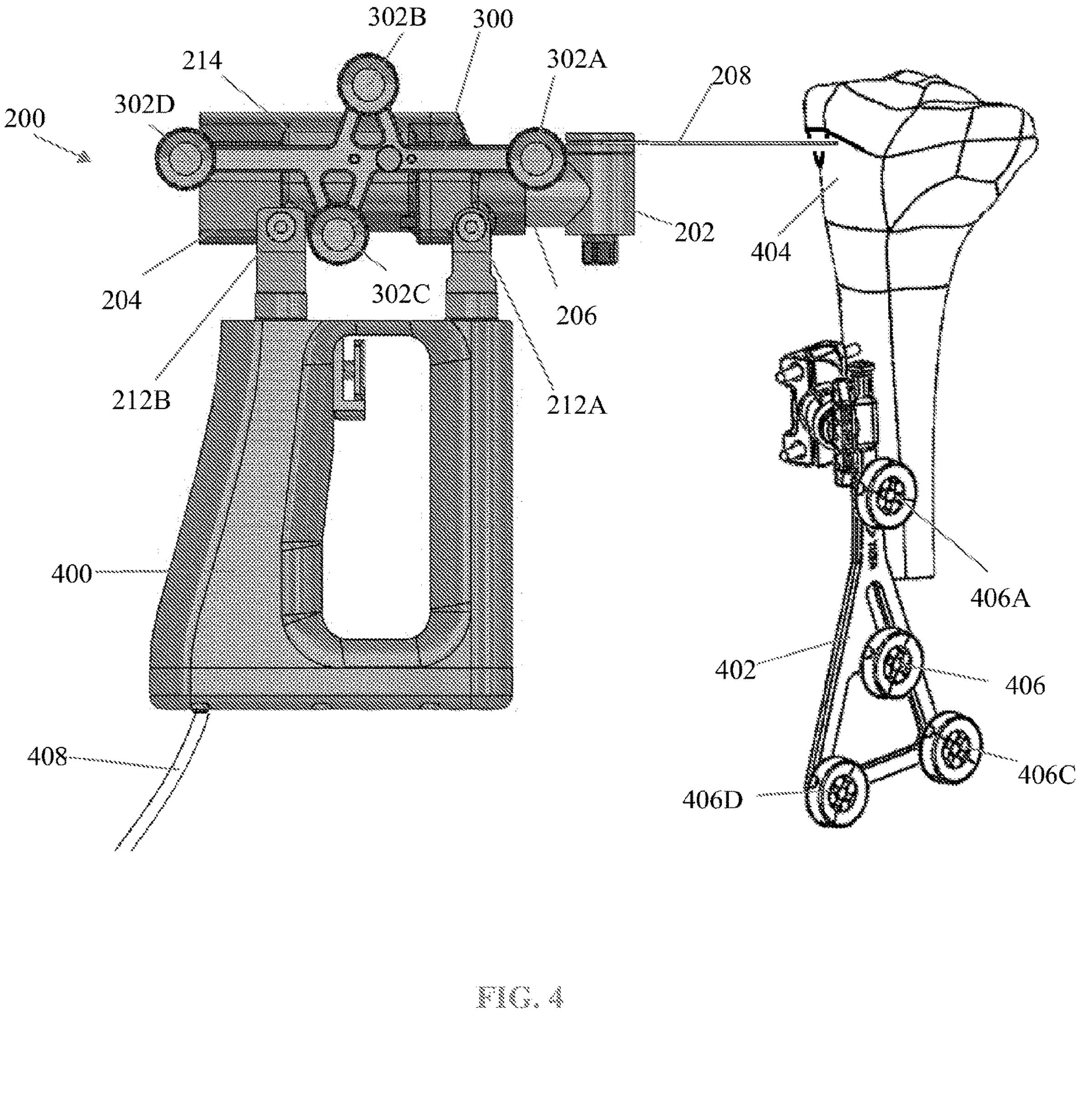
FIG. 4 depicts the surgical resection device of FIG. 3 with a handle and as part of a navigation system including an optical tracking system coupled to patient anatomy to be resected in accordance with an embodiment.

Referring to FIG. 4, the surgical resection device 200 is illustrated with a handle 400 and as part of a navigation system including an optical tracking system 402 coupled or fixed to patient anatomy 404 to be resected in accordance with an embodiment of this technology. The handle 400 in this example is coupled to the static housing 204 and provides a housing for the linear actuators 210A-B and pinned linkages 212A-B while providing a form factor that facilitates handheld operation of the surgical resection device 200. In some embodiments, at least one of the linkages 212A-B is slotted to allow less constrained movement of the tool. Alternatively, in an example, one of the linear actuators 210A-B may not be pinned, but instead moves only in one axis. In some examples the housing includes a trigger. In some examples, the housing includes a gap between the linear actuators 210A-B. In further examples, the gap is configured to fit the operator's fingers.

The optical tracking system 402 in this example includes a plurality of markers or fiducials 406A-D that allow the surgical computer 150 or other navigation or tracking device within the CASS 100 to determine the position and orientation of the patient anatomy 404. Accordingly, the optical tracking devices 300 and 402 facilitate relative determination of position and orientation within an operating environment to align the resection tool 202 of the surgical resection device 200 with a resection plane associated with the patient anatomy 404.

In the example of FIG. 4, the tracking device 300 is coupled to the static housing 204. In other examples, the tracking device 300 is coupled to the handle 400. In further examples, a tracking device is coupled on multiple locations on the surgical resection device 200, such as on both sides of the static housing 204 and/or the handle 400. Multiple tracking devices can allow the surgical resection device 200 to continue to operate (i.e., maintain visibility of at least one tracking device by the tracking system 115) when the surgeon changes position and/or inverts the surgical resection device 200.

In further examples, the surgical resection device 200 can include a physical guide (not shown) statically affixed to the handle. The physical guide can reflect the natural plane and/or position of the cutting edge given no correction from the linear actuators 210A-B and/or motor 214. The surgical resection device 200 can include one or more indices depicting the current correction provided by the linear actuators 210A-B and/or motor 214 in comparison to the physical guide. In an example, the indices depict a maximum corrective capability.

In the example of FIG. 4, the surgical resection device 200 is coupled to a surgical computer 150 and/or another device with the CASS 100 via an electrical connection 408. In particular, the electrical connection 408 is coupled to the linear actuators 210A-B and/or motor 214 to facilitating control or driving of those components by the surgical computer 150, as will now be described in more detail with reference to FIG. 5.

Figure 5:
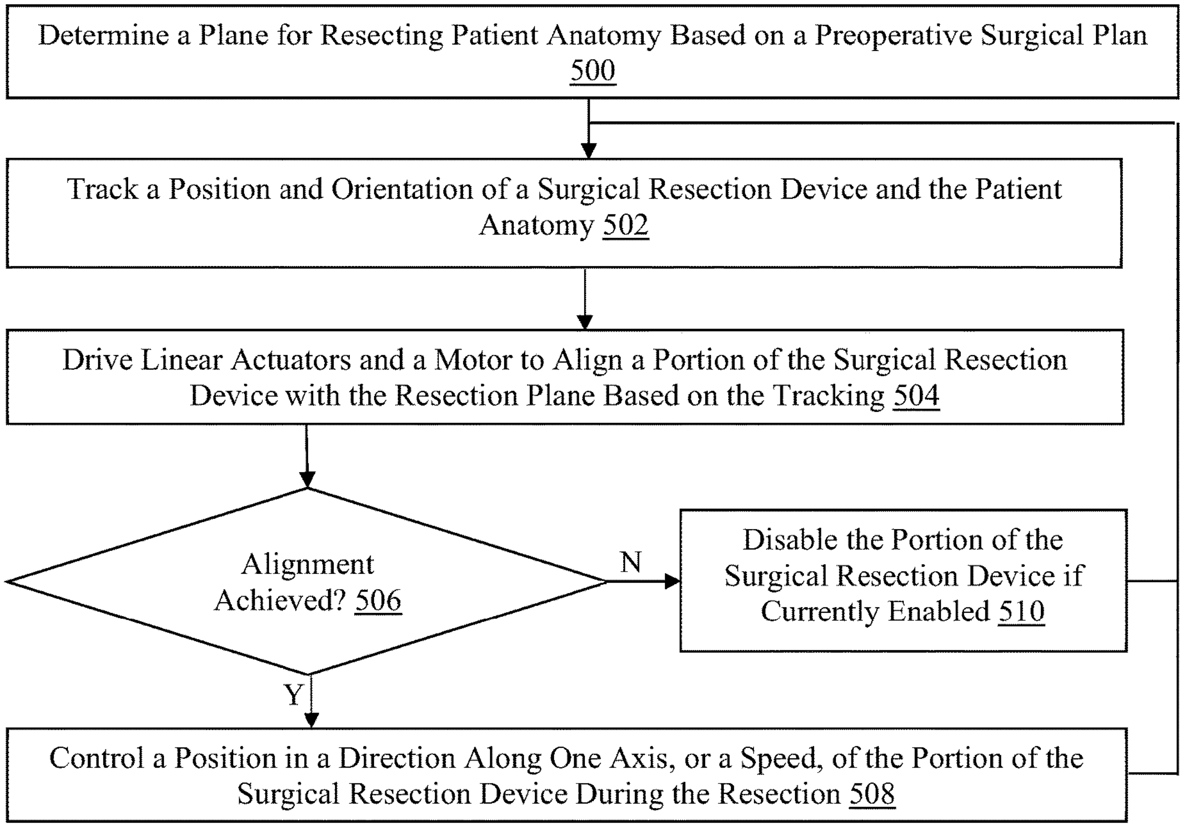
FIG. 5 depicts a flowchart of an illustrative method for facilitating resection during a surgical procedure in accordance with an embodiment.

Referring to FIG. 5, a flowchart of an illustrative method for facilitating resection during a surgical procedure in accordance with an embodiment of this technology is illustrated. The degrees of freedom detailed above allow the resection tool 202 of the surgical resection device 200 to be automatically repositioned relative to the anatomy 404 to be resected, such as a femur or tibia to facilitate the placement of implant(s) as part of a knee arthroplasty. With the surgical resection device 200 described and illustrated herein, a surgeon can roughly align the resection tool 202 while robotic assistance via the surgical computer 150 can fine tune the position and orientation of the saw blade 208 to align with the intended resection plane while the bone cuts are executed in accordance with a surgical plan.

In some examples, the optical tracker devices 300 and 402 tracked by the CASS 100 are rigidly affixed to the surgical resection device 200 and patient anatomy 404, respectively, and the location of the saw blade 208, for example, relative to the optical tracker device 300 is known. Accordingly, the surgical computer 150 can communicate with the linear actuators 210A-B and/or motor 214 to align the saw blade 208, for example, to the intended resection plane determined from a preoperative surgical plan based on tracking of the optical tracker device(s) 300 and 402.

In particular, based on the tracking, the surgical computer 150 can advantageously drive the linear actuators 210A-B and/or motor 214 to change the position and/or orientation of the resection tool 202 and associated saw blade 208 to maintain the appropriate alignment to the resection plane. If the saw blade 208, for example, is unable to align onto the resection plane, the saw blade can be stopped, preventing unintended cutting of the patient anatomy 404. Accordingly, the surgical computer 150 can control the cutting speed of the resection tool 202 in addition to the position and orientation of the resection tool within the activated degrees of freedom.

More specifically, in step 500 in this example, the surgical computer 150 determines a resection plane for resecting patient anatomy 404 based on a preoperative surgical plan for an associated surgical procedure. The resection plane can be a desired or intended cut plane for resecting bony anatomy to facilitate the attachment of an implant, for example. The surgical plan can be generated based on preoperative imaging of the patient anatomy 404 and can define the resection plane as well as other aspects of the surgical procedure.

In step 502, the surgical computer 150 tracks a position and orientation of the surgical resection device 202 and the patient anatomy 404 during the surgical procedure based on the optical tracking devices 300 and 402, respectively, in this example. In other examples, the tracking can be accomplished using image tracking, electromagnetic tracking, radar-based tracking, and/or accelerometer(s) or inertial measurement unit(s), or any other type of surgical tracking technology.

In step 504, the surgical computer 150 drives one or more of the motor 114 or one or more of the linear actuators 210A-B to attempt to align a portion of the resection tool 202 (e.g., the saw blade 208) with the resection plane determined in step 500 based on the positions and orientations tracked in step 502. Accordingly, the surgeon initiates relatively rough repositioning of the handheld surgical resection device 200 while the more granular alignment of the saw blade 208, for example, is controlled by the surgical computer 150 that drives the motor 114 and/or linear actuator(s) 210A-B based on a tracked position and orientation of the surgical resection device and the resection tool 202 coupled thereto.

In some examples, the relatively less granular motion is guided to assist the surgeon with respect to achieving a more optimal pose of the handle 400 and resection device 200. In these examples, based on the plane determined in step 500 and the tracking in step 501, the surgical computer 150 can provide an output that includes indications of suggested movements to assist the surgeon. For example, the output can be activation of LEDs attached to glasses worn by the surgeon or real-time video data introduced into a display of a head-mounted display (HMD) system. The video data can include representations of the resection device 200 and patient anatomy with guidance indication introduced into the video feed, for example. In another examples, a dial or other graphical display can be presented in the HMD that illustrated the existing rotation or position of the resection tool 200 and/or the desired rotation or position, for example. Other types of guidance systems can also be used in other examples.

In step 506, the surgical computer 150 determines whether an alignment with the resection plane has been achieved by the cutting element (e.g., saw blade 208) of the resection tool 202. The determination in step 506 can be based on an alignment threshold, tolerance indicative of the ability of the saw blade 208 to align with the resection plane based on one or more of the linear actuators 210A-B being positioned at the limit of their travels, or the visibility of a tracking device, although other methods for determining satisfaction of the condition in step 506 can also be used. If the surgical computer 150 determines in step 506 that an alignment has been achieved, then the Yes branch is taken to step 508.

In step 508, the surgical computer 150 controls a position along one axis, such as the first axis (i.e., the Z axis illustrated in FIGS. 2-5), and/or a speed of the cutting element (e.g., saw blade 208) of the resection tool 202 during the resection of the patient anatomy 404. For example, upon achieving an initial alignment, the surgical computer 150 can control the speed of the saw blade 208 by initiating oscillation or otherwise enabling the saw blade. In another example in which the cutting element is a burr, the surgical computer 150 can initiate rotation of the burr (e.g., based on communication with the motor 214) upon achieving an alignment of an axis of the burr with the resection plane.

In other examples, the position of the cutting element can be controlled in the direction of the first axis (i.e., the Z axis illustrated in FIGS. 2-5) by extending or limiting oscillation travel of the saw blade 208. In another example, the surgical computer 150 can control the position of the cutting element in the direction of the first axis (i.e., the Z axis illustrated in FIGS. 2-5) by retracting the saw blade 208 into, or extending the saw blade from, a sleeve (not shown) disposed within the static housing 204 of the surgical resection device 200. In yet other examples, a fourth degree of freedom is provided that controls the width of the cut introduced by the cutting element (i.e., the angle through which the saw blade 208 oscillates). Accordingly, in these examples, the position of the cutting element can be controlled by the resection tool 202 in a plane formed by the X and Z axes illustrated in FIGS. 2-5.

The surgical computer 150 can also control the position of the cutting element in the direction of the first axis (i.e., the Z axis illustrated in FIGS. 2-5) by retracting or extending a burr to control an exposure of the burr. The extension or retraction of the cutting element can be controlled by the motor 214 or another actuator disposed proximate the static housing 204, for example.

Other methods for controlling the position of the cutting element (e.g., the saw blade 208) can also be used in other examples. Subsequent to controlling the position and/or speed of the cutting element, the surgical computer 150 proceeds back to step 502 and continues the tracking described and illustrated in detail above. Accordingly, the surgical computer 150 in some examples continuously tracks the position and orientation in step 502, drives the linear actuator(s) 210A-B and motor 214 to attempt to maintain an alignment of the saw blade in step 504, and controls the position and/or speed of the saw blade in step 508 unless an alignment is no longer achieved and the condition in step 506 is not satisfied. If the surgical computer 150 determines in step 506 that an alignment with the resection plane is not currently achieved, then the No branch is taken to step 510.

In step 510, the surgical computer 150 disables the cutting element (e.g., saw blade 208) of the surgical resection device 200 if it was enabled upon the failure of the condition in step 506. If the surgical computer 150 is unable to adequately control the position and/or rotation of the saw blade 208 in some examples, such as due to a limitation in the travel of a particular mechanism (e.g., one or more of linear actuator 210A-B), the saw blade may be stopped at, or just before breaching, a virtual cut plane to prevent an unintended resection of the patient anatomy 404. Optionally, an audible or visual indication of the misalignment can be output by the surgical resection device 200 and/or other actions can also be taken in step 510. Subsequent to disabling the saw blade 208 of the resection tool 202 in step 510 in this example, the surgical computer 150 proceeds back to step 502 and continues to track the surgical resection device 200 and drive the linear actuator(s) 210-B and/or motor 214 in step 504 until an alignment is again achieved and the condition in step 506 is satisfied.

In some examples, the cutting motion of the surgical resection device 200 is configured to slow or deactivate based on a threshold velocity of user-initiated movement associated with the device 200. For example, if a surgeon were to move the surgical resection device 200 faster than a determined threshold of correction, the device 200 can deactivate to prevent damage to the patient anatomy.

In some examples, the surgical resection device 200 is coupled to one or more input devices for controlling the surgical resection device 200. In an example, at least one of the input devices is located on the surgical resection device 200 (e.g., triggers or buttons). In another example, at least one of the input devices is external to the surgical resection device 200 (e.g., foot pedals or a graphical user interface). An input device may be used for some combination of activating the cutting edge of the resection on the device 200, deactivating the cutting edge of the resection on the device 200, enabling some combination of the linear actuators and motor, disabling some combination of the linear actuators and motor.

The examples provided herein have focused on use cases of the device including resection; however, this is merely for illustrative purposes and the device 200 can be applicable for many uses cases requiring alignment in a surgical environmental. As an example, the device 200 can be used to align a cut guide or implant using similar methodologies as described herein. An interface can removably attach a cut guide and/or implant to the device 200.

Figure 6:
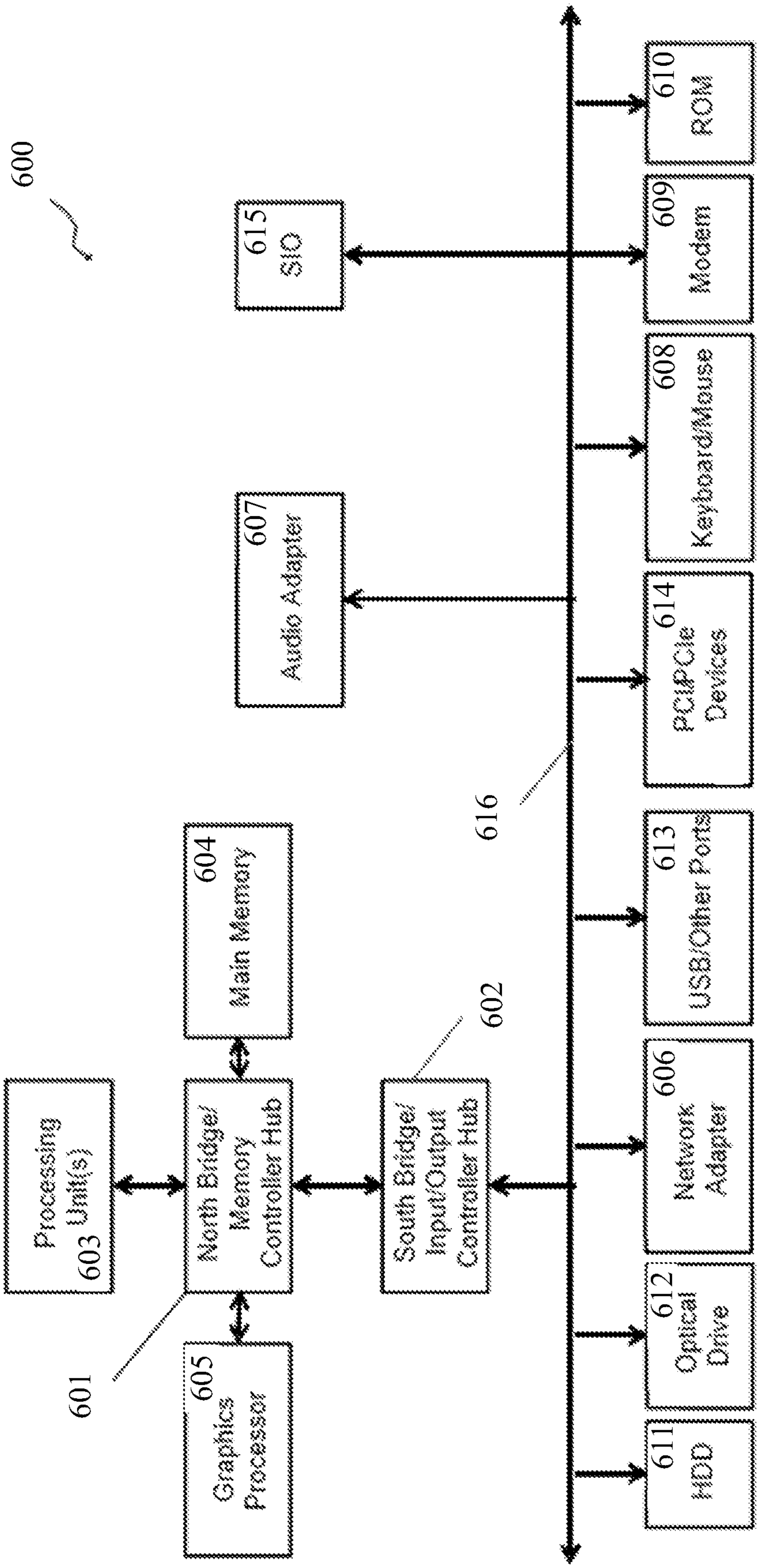
FIG. 6 depicts a block diagram of an illustrative surgical computing device in which aspects of the illustrative embodiments are implemented.

FIG. 6 illustrates a block diagram of an illustrative data processing system 600 in which aspects of the illustrative embodiments are implemented. The data processing system 600 is an example of a computer, such as a server or client, in which computer usable code or instructions implementing the process for illustrative embodiments of the present invention are located. In some embodiments, the data processing system 600 may be a server computing device. For example, data processing system 600 can be implemented in a server or another similar computing device operably connected to a CASS 100 as described above. The data processing system 600 can be configured to, for example, transmit and receive information related to a patient and/or a related surgical plan with the CASS 100. Accordingly, the data processing system 600 can be the surgical computer 150, integral with the surgical computer, or communicably coupled to the surgical computer 150 in some examples.

In the depicted example, data processing system 600 can employ a hub architecture including a north bridge and memory controller hub (NB/MCH) 601 and south bridge and input/output (I/O) controller hub (SB/ICH) 602. Processing unit 603 (e.g., one or more central processing units or processor cores), main memory 604, and graphics processor 605 can be connected to the NB/MCH 601. Graphics processor 605 can be connected to the NB/MCH 601 through, for example, an accelerated graphics port (AGP).

In the depicted example, a network adapter 606 connects to the SB/ICH 602. An audio adapter 607, keyboard and mouse adapter 608, modem 609, read only memory (ROM) 610, hard disk drive (HDD) 611, optical drive (e.g., CD or DVD) 612, universal serial bus (USB) ports and other communication ports 613, and PCI/PCIe devices 614 may connect to the SB/ICH 602 through bus system 616. PCI/PCIe devices 614 may include Ethernet adapters, add-in cards, and PC cards for notebook computers. ROM 610 may be, for example, a flash basic input/output system (BIOS). The HDD 611 and optical drive 612 can use an integrated drive electronics (IDE) or serial advanced technology attachment (SATA) interface. A super I/O (SIO) device 615 can be connected to the SB/ICH 602.

An operating system can run on the processing unit 603. The operating system can coordinate and provide control of various components within the data processing system 600. As a client, the operating system can be a commercially available operating system. An object-oriented programming system, such as the Java™ programming system, may run in conjunction with the operating system and provide calls to the operating system from the object-oriented programs or applications executing on the data processing system 600. As a server, the data processing system 600 can be an IBM® eServer™ System® running the Advanced Interactive Executive operating system or the Linux operating system. The data processing system 600 can be a symmetric multiprocessor (SMP) system that can include a plurality of processors in the processing unit 603. Alternatively, a single processor system may be employed.

Instructions for the operating system, the object-oriented programming system, and applications or programs are located on storage devices, such as the HDD 611, and are loaded into the main memory 604 for execution by the processing unit 603. The processes for embodiments described herein (e.g., with reference to FIGS. 2-6) can be performed by the processing unit 603 using computer usable program code, which can be located in a memory (e.g., a non-transitory computer readable medium portion thereof) such as, for example, main memory 604, ROM 610, or in one or more peripheral devices.

A bus system 616 can be comprised of one or more busses. The bus system 616 can be implemented using any type of communication fabric or architecture that can provide for a transfer of data between different components or devices attached to the fabric or architecture. A communication unit such as the modem 609 or the network adapter 606 can include one or more devices that can be used to transmit and receive data.

As described and illustrated in detail above, this technology provides a relatively small form factor for a surgical resection device that is relatively inexpensive and minimally disruptive to surgical procedures as compared to a fully autonomous robotic-assisted procedure. This technology advantageously facilitates reduced surgical procedure times as compared to fully autonomous robotic-assisted procedures, while maintaining the benefits of preoperative planning and implant placement accuracy that are typical with robotic-assisted procedures. Specifically, this technology facilitates more efficient bone resection without a decrease in accuracy with respect to resection plane or surface finish.

While various illustrative embodiments incorporating the principles of the present teachings have been disclosed, the present teachings are not limited to the disclosed embodiments. Instead, this application is intended to cover any variations, uses, or adaptations of the present teachings and use its general principles. Further, this application is intended to cover such departures from the present disclosure that are within known or customary practice in the art to which these teachings pertain.

In the above detailed description, reference is made to the accompanying drawings, which form a part hereof. In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 components refers to groups having 1, 2, or 3 components. Similarly, a group having 1-5 components refers to groups having 1, 2, 3, 4, or 5 components, and so forth.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by 1/10 of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the present disclosure include equivalents to the recited values, e.g., variations in the numerical quantity of such values that can occur, but would be recognized to be equivalents by a person skilled in the art.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

We claim:

1. A surgical computing device, comprising a non-transitory computer-readable medium comprising programmed instructions stored thereon for facilitating resection during a surgical procedure and one or more processors coupled to the non-transitory computer-readable medium and configured to execute the stored programmed instructions to:

determine a resection plane for resecting patient anatomy based on a preoperative surgical plan;

track a position and orientation of a surgical resection device during a surgical procedure, wherein the surgical resection device comprises a resection tool, a motor configured to rotate the resection tool about a first axis such that an element of the resection tool is movable to a fixed position around the first axis to allow a plurality of cut angles with respect to rotation of the motor, and at least two linear actuators independently drivable to translate the resection tool within a second axis and rotate the resection tool about a third axis;

drive one or more of the motor or one or more of the at least two linear actuators to align a portion of the resection tool with the resection plane based on the tracked position and orientation; and control a position of the portion of the resection tool in a direction of the first axis, or a speed of the portion of the resection tool, based on the tracked position and orientation during resection of the patient anatomy.

2. The surgical computing device of claim 1, wherein the resection tool comprises a surgical saw, wherein the portion of the surgical saw comprises a saw blade.

3. The surgical computing device of claim 2, wherein the one or more processors are further configured to execute the stored programmed instructions to initiate oscillation of the saw blade when an alignment of the saw blade with the resection plane is determined to be achieved based on the tracked position and orientation.

4. The surgical computing device of claim 2, wherein the one or more processors are further configured to execute the stored programmed instructions to enable or disable oscillation of the saw blade to control the position of the saw blade in the direction of the first axis.

5. The surgical computing device of claim 2, wherein the one or more processors are further configured to execute the stored programmed instructions to extend or limit oscillation of the saw blade to control the position of the saw blade in the direction of the first axis.

6. The surgical computing device of claim 2, wherein the one or more processors are further configured to execute the stored programmed instructions to retract the saw blade into, or extend the saw blade from, a sleeve disposed within a static housing of the surgical resection device to control the position of the saw blade in the direction of the first axis.

7. The surgical computing device of claim 6, wherein the resection tool and the motor are disposed proximate opposing ends of the static housing and interface within the static housing via an annular gear of the resection tool and a pinion gear of the motor, wherein the processors are further configured to execute the stored programmed instructions to drive the motor to rotate the pinion gear to cause the pinion gear to engage the annular gear to rotate the resection tool about the first axis.

8. The surgical computing device of claim 1, wherein the one or more processors are further configured to execute the stored programmed instructions to track the position and orientation relative to the patient anatomy based on a first optical tracking device coupled to the surgical resection device and a second optical tracking device coupled to the patient anatomy, wherein each of the first and second optical tracking devices comprises a plurality of fiducials.

9. The surgical computing device of claim 1, wherein the resection tool comprises a burr, wherein the processors are further configured to execute the stored programmed instructions to initiate rotation of the burr when an alignment of the burr with the resection plane is determined to be achieved based on the tracked position and orientation.

10. The surgical computing device of claim 9, wherein the one or more processors are further configured to execute the stored programmed instructions to extend or retract the burr in the direction of the first axis to control an exposure of the burr.

11. The surgical computing device of claim 1, wherein the one or more processors are further configured to execute the stored programmed instructions to control a width of a cut by the resection tool with respect to a plane perpendicular to the first axis by varying an oscillation angle of the resection tool.

* * * * *